US005272255A

United States Patent [19]
Delespesse

[11] Patent Number: 5,272,255
[45] Date of Patent: Dec. 21, 1993

[54] POLYPEPTIDE FACTORS FROM COLOSTRUM

[75] Inventor: Guy Delespesse, Winnipeg, Canada

[73] Assignee: Ciba-Geigy Corporation, Ardsley, N.Y.

[21] Appl. No.: 872,203

[22] Filed: Apr. 22, 1992

Related U.S. Application Data

[62] Division of Ser. No. 376,086, Jul. 6, 1989, which is a division of Ser. No. 819,557, Jan. 17, 1986, Pat. No. 4,866,037.

[30] Foreign Application Priority Data

Jan. 26, 1985 [GB] United Kingdom ............... 8502006

[51] Int. Cl.$^5$ .................... C07K 15/06; C07K 15/14
[52] U.S. Cl. ................... 530/350; 530/395; 530/832; 530/862; 530/868
[58] Field of Search ............... 530/350, 387, 395, 832

[56] References Cited

U.S. PATENT DOCUMENTS

| | | | |
|---|---|---|---|
| 3,553,317 | 1/1971 | Michaelson et al. | 424/87 |
| 4,644,056 | 2/1987 | Kothe et al. | 530/387 |
| 4,866,037 | 9/1989 | Delespesse | 514/8 |
| 5,081,028 | 1/1992 | Hofstetter et al. | 435/172.3 |

FOREIGN PATENT DOCUMENTS

| | | |
|---|---|---|
| 155192 | 9/1985 | European Pat. Off. |
| 205405 | 12/1986 | European Pat. Off. |
| WO81/00813 | 4/1991 | PCT Int'l Appl. |

OTHER PUBLICATIONS

Head et al., *Transplantation Proceedings*, 9:1465–1471 (1977).
Beer et al., Transplant Proc., 7:399 (1975).
Deguchi et al., *J. Immunol.*, 131(6):2751–2756 (1983).
Zuraw et al., *J. Immunol.*, 127(3):1169–1177 (1981).
Ishazaka, *Ann. Rev. Immunol.*, 2:159–182 (1984).
Katz et al., Regulation of IgE Antibody System in Humans and Experimental Animals in: *Progress in Immunology*. 5th ed., Y. Yamamura & T. Toda, Acad. Press (1983) pp. 465–482.
Sarfati et al., *Immunology*, 53:197–204 (1984).
Huff et al., *PNAS USA*, 81:1514–1518 (1984).
Sandberg et al., IgE–Binding Factors in Atopic Eczema in: *Proceed. of XI Int. Congress Allergy Clin. Immunol.*, Macmillan Press Ltd., 1983, pp. 105–108.
Schlesinger et al., *The Lancet*, 2:529–532 (1977).
Mohr, J. Pediat., 82:1062–1064 (1973).
Cruz, et al., *J. Pediat.*, 93:600–602 (1981).
Frick et al., *J. Allergy Clin. Immunol.*, 63:228–241 (1979).
Crago et al., *Surv. Immunol. Res.*, 2:164–169 (1983).
Kjellman et al., *Annals of Allergy*, 53:167–171 (1984).
Jarret et al., *Nature*, 280:145–147 (1973).
Roberts et al., *Immunology*, 48:195–199 (1983).
Richie et al., *J. of Immunol.*, 129:1116–1119 (1982).
Parmely et al., *J. Exp. Med.*, 144:358–370 (1976).
Jarrett, *The Lancet*, 797–798 (1984).
Jarrett et al., Immunology, 53:365–373 (1984).
Jarrett et al., *Immunology*, 48:49–58 (1983).
Mestecky et al., *Chem. Abstr.*, 95:113219h (1986).

*Primary Examiner*—Michael G. Wityshyn
*Assistant Examiner*—Choon Koh
*Attorney, Agent, or Firm*—Michael W. Glynn

[57] ABSTRACT

IgE binding factors (IgE-bfs) with IgE suppressor (IgE-SF) activity obtainable from human colostrum in an enriched form, a method for the prevention and/or the treatment of allergy by administering the IgE-bfs and pharmaceutical compositions comprising said IgE-bfs.

5 Claims, No Drawings

POLYPEPTIDE FACTORS FROM COLOSTRUM

This is a divisional of Ser. No. 07/376,086, filed Jul. 6, 1989, which is a divisional of Ser. No. 06/819,557, filed Jan. 17, 1986, now U.S. Pat. No. 4,866,037.

FIELD OF THE INVENTION

The invention concerns novel polypeptide factors from human colostrum with affinity for IgE antibodies (IgE-binding factors) and capable of suppressing the synthesis of IgE antibodies by lymphocytes (IgE suppressor activity), methods for isolating these factors and their use in the treatment of allergy.

The following abbreviations are used in this specification:

| | |
|---|---|
| IgE | — immunoglobulin E |
| IgG | — immunoglobulin G |
| IgE-bfs | — IgE-binding factors, polypeptides binding to IgE anti-bodies |
| IgE-SFs | — IgE-suppressor factors, polypeptides suppressing the synthesis of IgE antibodies by B lymphocytes |
| IgE-PFs | — IgE-potentiating factors, polypeptides potentiating, i.e. enhancing the synthesis of IgE antibodies by B lymphocytes |
| IgA | — immunoglobulin A |
| IgM | — immunoglobulin M |
| GIF | — glycosylation inhibiting factor |
| GEF | — glycosylation enhancing factor |
| KD | — kilo Dalton, 1KD = 1000 g/Mol |
| MW | — molecular weight |
| M | — molar |
| E-IgE | — erythrocytes coated with IgE |
| RPMI 8866 | — a B lymphocyte cell line expressing FcR |
| Tris | — tris(hydroxymethyl)aminomethane |
| BSA | — bovine serum albumin |
| HBSS | — Hanks' balanced salt solution |
| IgE-PS | — human IgE of myeloma PS |
| E-IgE-RFC | — cells forming rosettes with IgE-coated erythrocytes |
| SD | — standard deviation |

BACKGROUND OF THE INVENTION

Allergic diseases are a major health problem as a very great number of individuals are affected thereby. Usually the therapy is restricted to the use of antihistamines or to more or less effective immunization procedures. The classical antiallergic drugs have certain disadvantages, especially since they cause various side effects in the treated patient. The immunization procedure is limited to one or two allergens whereas most of the patients are sensitive to a large number of allergens. In addition, hyposensitization treatment is neither curative nor protective. As it is known that IgE plays a major role in allergic diseases, the mechanisms regulating the production of IgE have been extensively investigated during the last ten years. These studies have demonstrated the existence in animal models of several factors controlling the synthesis of IgE. Such factors are produced by B and T lymphocytes and have been named: suppressing factor of allergy (SFA), suppressive effector molecules (SEM), IgE-induced regulants from B or T cells (EIR$_B$ and EIR$_T$) IgE-binding factors (IgE-BFs), glycosylation enhancing factors (GEF), and glycosylation inhibiting factors (GIF).

Some of the factors are definitely different from each other on account of their molecular weights and/or biological activities (for review see references 1 and 2).

The role of IgE-binding factors (IgE-bfs) in the non-antigen specific regulation of IgE antibody production has been extensively investigated in animals (as reviewed in reference 1) where it was shown that IgE-bfs are the effector molecules of the IgE-specific isotype regulation. Two kinds of IgE-bfs differing mainly by their carbohydrate moieties were identified, i.e. IgE suppressor and IgE potentiating factors (IgE-SFs; IgE-PFs); the ratio between IgE-SFs and IgE-PFs determines the actual production of IgE antibodies. The same cells are capable of secreting either IgE-SFs or IGE-PFS depending on the influence of either glycosylation inhibiting or enhancing factors (GIF, GEF) which are secreted by distinct regulatory T lymphocyte subpopulations.

Human I&E-bfs have also been described recently in the culture supernatants of either T- or B-cell lines expressing receptors for IgE (3, 4) as well as in the serum of selected patients with severe atopic dermatitis (5). Further biochemical characterization of the IgE-bfs of different origins is definitely required in order to determine whether or not they correspond to identical molecules.

It is already known that breast-feeding may alter the immune reactivity of the newborn. This was described in experimental animals (6) and in humans where it was shown, for example, that babies fed with milk from tuberculin sensitive mothers acquired cell-mediated immunity to tuberculin (7,8). Recent prospective studies further indicated that exclusive breast-feeding protects the high risk infants against allergic disease.

Multiple mechanisms were invoked to explain the latter observations: (i) a reduced exposure to foreign food antigens, (ii) the protection by milk IgA blocking antibodies specific to various alimentary antigens and to other environmental antigens (9), (iii) the protection against common viral diseases known to trigger the onset of allergic diseases (10) and finally (iv) the presence in human milk of immunoregulatory factors capable of modulating the immature immune system of the neonate (11). It is also known that newborns with a high risk for allergic diseases can be identified on the basis of family history and of high IgE levels in the cord blood serum (12).

The well documented observation on the immunoreactivity of breast-fed newborns might be explained by the presence in human colostrum of specific antibodies or idiotypes (13, 14), immunoregulatory factors, or regulatory lymphocytes (15, 16). Hence, it is suggested that breast-feeding may protect newborns by providing them with either IgE-suppressor factors, or with other molecules (such as GIF) or cell's capable of interfering with the infants lymphocytes involved in the regulation of IgE antibody production.

So far IgE-bfs with IGE-SF activity have not been identified in human colostrum, and the isolation thereof is nowhere described. Surprisingly, such IgE-bfs have now been isolated.

OBJECT OF THE INVENTION

A first object of the present invention is to provide IgE-bfs with IgE-SF activity from human colostrum and a method for their isolation.

A further object of this invention is to provide a method for the prevention and/or the treatment of allergy by administering the IgE-bfs of the present invention, and to provide pharmaceutical compositions comprising said IgE-bfs.

DETAILED DESCRIPTION OF THE INVENTION

The present invention concerns IgE binding factors (IgE-bfs) with IgE suppressor (IgE-SF) activity obtainable from human colostrum in an enriched form.

The IgE-bfs of the present invention are further characterized as follows: (1) they are polypeptides having a molecular weight of between 10 and 25 kilo-daltons (KD), as determined by chromatography on a calibrated Sephadex G75 column; (2) they block the binding of IgE to cells bearing receptors for IgE, e.g. as determined by inhibiting the rosetting of RPMI 8866 cells with E-IGE; (3) they suppress in a dose dependent fashion the synthesis of IgE without altering the production of IgM by B lymphocytes of allergic human donors; (4) they bind to IgE, e.g. as determined by their adsorption to IgE-Sepharose, and they do not bind to IgG, e.g. as determined by their lack of adsorption to IgG-Sepharose; (5) in Western blot assays, colostrum IgE-bfs are identified as one band capable of binding specifically to radiolabelled IgE and not to labelled IgG, IgH or IgA; the apparent molecular weight of colostrum IgE-bfs is 14–16 KD; (6) the biologic acticity of the factors is resistant to ebullition, i.e. they still bind $^{125}$I-IgE after boiling for 3 min in the presence of SDS (sodium dodecyl sulfate).

The IgE-bfs of the present invention are contained in human colostrum preparations in higher than natural concentration. They may still be admixed with other human colostrum polypeptides of similar or higher molecular weight, for example of up to about 45 or 50 KD, however they are essentially free of other non-polypeptide ingredients of human colostrum. Preferably the IgE-bfs are free of polypeptides with a molecular weight of below 10 and above 25, especially above 20 KD, and essentially free of other non-polypeptide ingredients of human colostrum.

The process for the preparation of the IgE-bfs of the present invention is characterised in that human colostrum is used as starting material and that the IgE-bfs are enriched up to a higher than natural concentration.

More particular, human colostrum from healthy volunteers is collected during the first two days of postpartum, however milk collected later may also be used. The colostrum is first clarified, e.g. by ultracentrifugation, and then acidified, e.g. with hydrochloric acid, up to about pH 4 in order to precipitate the casein. After removing the casein, e.g. by filtration or centrifugation, the clarified preparation is neutralized, e.g. with 2M Tris buffer, and passed through a filter system, preferably stepwise, in order to remove large molecules of over 50 KD. For example, the pores of the first filter may have a diameter of about 0.45 $\mu$M, and the filtrate thereof may than be passed through a membrane filter, e.g. Amicon XM 50, with the desired cut-off point of 50 KD. After filtration the preparation is dialyzed against distilled water and lyophilized.

The lyophilisate is preferably further purified by chromatographic methods to collect the polypeptides with a molecular weight of between about 10 and 25 KD. Any conventional (chromatographic method may be used, such as agarose plate gel chromatography or column chromatography, e.g. on Sephadex 675. The solvent is advantageously a buffer, e.g. containing sodium chloride (e.&;. 40 Mm), Tris HCl (e.g. 10 mM of pH 8.0), a surface active compound (e.g. 0.05 % Tween 20), an amino acid (e.g. 10 mM epsilon aminocaproic acid), and a protein (e.g. 0.1 % bovine serum albumine BSA). The fractions containing the IgE-bf are those containing polypeptides of a molecular weight of about 10 to 25 KD. They are pooled, concentrated, e.g. in vacuum, and dialyzed, e.g. against Hanks' balanced salt solution (HBSS).

It should be understood that any other conventional method of isolating the IgE-bfs is comprised by the present invention.

The IgE-bfs can be further purified by conventional methods, such as isoelectric focussing, or via monoclonal antibodies.

The IgE binding and IgE synthesis suppressing activity of the isolated IgE-bfs can be determined by methods known in the art, e.g. by the rosette inhibition assay, affinity chromatography experiments, and experiments measuring the suppression of the ongoing in vitro IgE synthesis by lymphocytes from allergic individuals (3).

The adsorption and elution experiments on IgE- and IgG-Sepharose 4B can be taken as specificity controls indicating that the rosette inhibition activity of colostrum is indeed due to factors having affinity for IgE.

Most interestingly, the present data indicate that colostrum suppresses the in vitro synthesis of human IgE and that this suppression is mediated by IgE-bfs. Indeed, IgE-bfs and IgE-suppressing activity were both specifically absorbed on IgE-Sepharose. The colostrum preparations have no effect on IgM synthesis.

The invention further concerns the use of the novel IgE-bfs of the present invention for the treatment or prevention of allergic conditions in patients being allergic against all kinds of antigens, for example pollens, cat danders, house dust mites, and the like. Particular important would be the treatment of high risk patients during critical periods, including especially high risk new-borns which are not breast-fed. The IgE-bfs of the present invention are administered enterally, for example nasally, rectally or orally, or parenterally, for example, intramuscularly, subcutaneously or intravenously, usually in dosage unit forms such as tabletts, dragees, ampoules, vials, suppositories. The amount of IgE-bfs of the present invention to be administrated depends on the weight and general condition of the patient, the severity of the disease, the mode of administration and has to be based on the judgement of the physician. In general a dose of between about 100 and about 5000 $\mu$g per kg bodyweight and day may be administered.

The invention further concerns pharmaceutical preparations containing the IgE-bfs of the present invention in an antiallergically effective amount optionally in conjunction with conventional pharmaceutically acceptable carriers, that are suitable for oral or parenteral, i.e. intramuscular, subcutaneous or intraperitoneal, administration and that do not deleteriously interact with the active ingredients.

There are suitable tablets, capsules, vials containing a solid powder, or vials, ampoules and the like containing infusion solutions, preferably aqueous solutions or suspensions, it being possible to prepare these before use, for example from lyophilized preparations that contain the active ingredient alone or together with a carrier, such as mannitol, lactose, glucose, albumin and the like. The pharmaceutical preparation may be sterilized and, if desired, mixed with adjuncts, for example preservatives, stabilisers, emulsifiers, solubilisers, buffers and/or salts for regulating the osmotic pressure. Sterilization can be achieved by sterile filtration through filters of small pore size (0.45 $\mu$m diameter or smaller) after which the preparation can be lyophilized, if desired. Antibiotics may also be added in order to assist in preserving sterility.

The pharmaceutical preparations according to the present invention are dispensed in unit dosage forms, for example ampoules, comprising 1 to 2000 mg of a pharmaceutically acceptable carrier per unit dosage and about 1 to 100 mg, preferably about 5 to 50 mg, of the active ingredient (e.g. lyophilized colostrum preparation containing IgE-bf) per unit dosage.

The invention also concerns a method for producing a pharmaceutical preparation characterised in that a biologically active protein of the present invention is admixed with a pharmaceutically acceptable carrier.

The pharmaceutical preparations are produced in a manner known per se, for example by conventional mixing, dissolving, lyophilising and the like processes and contain from about 0.1 % to 100 %, especially from about 1 % to 50 % of the active substances.

The use of the new proteins for the prophylactic and therapeutic treatment of the human body is also an object of the present invention.

The following examples describe the present invention in more detail, however, they should not be construed as a limitation thereof.

EXAMPLE 1

Colostrum is collected from 15 unselected healthy volunteers during the first two days of postpartum. Samples are lit frozen immediately at $-20°$ C. Five pools, made of 3 samples each, are processed in parallel. They are first clarified by ultracentrifugation and then acidified (pH 4.0) with hydrochloric acid in order to precipitate the casein, the casein is removed and the clear preparations are then neutralized with 2M Tris and passed through a 0.45 μm filter. After filtration through Amicon XM50 membranes (MW cut-off 50 KD) the samples are dialyzed against distilled water and lyophilized. This material is referred to later as "colostrum preparation". In the gel filtration assays, 40 mg of lyophilized colostrum dissolved in 1.5 ml buffer (40 Mm NaCl, 10 Mm Tris HCl, pH 8.0 containing 0.05 % Tween 20, 10 mM epsilon aminocaproic acid and 0.1 % BSA) is applied on a calibrated Sephadex G75 column (2.5×90 cm). Fractions corresponding to molecular weight comprised between 10–15, 15–20, 20–25, 25–30, 30–45 and 45–60 KD are pooled, concentrated to 1.5 ml and dialyzed against Hanks' balanced salt solution (HBSS).

Fractions with polypeptides of molecular weight 10–20 KD contain the IgE-bf as shown by immunologic tests.

Immunologic Tests

The methods employed are exactly as previously described (3). IgE-bfs are detected by a rosette inhibition assay where RPMI 8866 cells, known to express surface receptors for IgE, are rosetted with bovine erythrocytes coated with a suboptimal concentration of purified IgE myeloma PS (a gift from Dr. K. Ishizaka, Johns Hopkins Univ., Baltimore, MD). When preincubated with IgE-coated erythocytes (E-IgE), IgE-bfs inhibit the binding of E-IGE to the RPHI 8866 cells. All the assays are performed in duplicate, the tubes are coded and the experimentator should ignore the codes. The experimental error is less than 15 %. Affinity chromatography experiments are performed exactly as mentioned in the previous studies (3) by employing highly purified IgE, such as IGE-PS, or polyclonal IgG-coupled to Sepharose 4B (4 mg protein/ml gel). Filtrates and eluates are concentrated to the initial volume of the sample and immediately neutralized and dialyzed against HBSS.

B lymphocytes are separated from the heparinized blood of allergic donors by centrifugation on Ficoll-hypaque; after adherence to plastic Petri dishes, the lymphocyte preparations are depleted of cells forming rosettes with AET (2-aminoethylisothiouronium hydrobromide) treated sheep red blood cells. Duplicate cultures containing 1 to 1.5×10$^6$ cells in 1.5 ml culture medium are performed in 24 well Linbro tissue culture plates. Some cultures are supplemented with cycloheximide (50 mcg/ml) and puromycin (10 mcg/ml) in order to determine the passive release of preformed IgE in the culture supernatant and to calculate the net IgE synthesis in the test cultures. The cultures are harvested after 7 days incubation at 37° C. in a water saturated atmosphere consisting of 92% air and 8% $CO_2$. Immunoglobulins are measured in the culture supernatants by a solid-phase radioimmunoassay. Two different mouse monoclonal antibodies are employed for the IgE measurements, i.e. clone 89 (prepared in our laboratory) and clone 4.15 (kindly supplied by Dr. A. Saxon, UCLA, Los Angeles, CA). The sensitivity of the assay is 0.1 ng/ml for IgE, 0.4 ng/ml for IgM and IgA and 0.8 ng/ml for IgG.

Western Blot Analysis: Eighty μl containing 100 μg of the colostrum preparation are incubataed overnight with 40 μl Laemmli buffer (containing 1 % SDS and 5 % 2-mercaptoethanol); the mixture is then run on 12 % SDS-PAGE (polyacrylamide gel electrophoresis); and transferred onto a nitrocellulose membrane. All the reagents and the equipment were from Bio-Rad Laboratories and the exact procedure was performed according to the Bio-Rad's instruction manual. After the transfer, the nitrocellulose membrane was exposed to radiolabelled IgE (10$^5$ cpm/ml; sp.act: 2×10$^4$/ng) for 24 hr and then processed for autoradiography by following the instruction manual.

RESULTS

Presence of IRE-bfs in Human Colostrum

The colostrum pools, prepared as described above, are tested at final concentrations ranging from 1 to 1000 mcg/ml for their ability to block the binding of IgE-coated bovine erytbrocytes (E-IgE) to IgE receptor bearing cells (RPMI 8866). Each colostrum preparation significantly inhibited the rosetting of RPMI 8866 cells with E-IgE, at optimal concentrations of 10 or 100 mcg/ml (Table Il). In order to demonstrate that the rosette inhibition is mediated by IgE-bfs, the colostrum fractions are adsorbed on IgE- or IgG-Sepharose. The results shown in Table I2 indicate that the rosette inhibiting activity is removed by absorption on IgE but not on IgG-Sepharose, suggesting that the inhibition is due to IgE-bfs present in colostrum. This is confirmed by showing that the rosette inhibiting activity can be recovered by acid elution (0.1 M glycine buffer, pH 2.8) of IgE-Sepharose but not of IgG-Sepharose. The molecular weight of IgE-bfs is estimated by gel filtration (Ex. 1) through a calibrated Sephadex C75 column. As shown in Table I3, IgE-binding activity is recovered in the fractions corresponding to MW ranging from 10 to 20 KD.

TABLE I

Influence of IgE-BF on IgE PS binding to RPMI 8866 cells

| Expt. # | Sample | % of cells forming rosette with E-IgE[a] | % rosette inhibition |
|---|---|---|---|
| 1 | Controll buffer | 70.6 ± 18[b] | — |
|   | Colostrum preparation (Ex. 13), 10 or 100 μg/ml | 48.6 ± 22[c] | 31.6 |
| 2 | Controll buffer | 81.9 ± 4.6[d] | — |
|   | Colostrum prep. (100 μg/ml) | 56.2 ± 6.1 | 35.8 |
|   | IgE-Sepharose, effluent[e] | 76.0 ± 2.6 | 6.5 |
|   | IgE-Sepharose, eluate | 59.5 ± 5.1 | 26.9 |
|   | IgG-Sepharose, effluent | 55.6 ± 3 | 36.7 |
|   | IgG-Sepharose, eluate | 83.7 ± 4 | 0 |
| 3 | Controll buffer | 47 ± 7[f] | — |
|   | Colostrum prep. (100 μg/ml) | 28 ± 4 | 41.5 |
|   | 10–15 KD[g] | 31 ± 7 | 34.1 |
|   | 15–20 KD | 29 ± 4 | 38.3 |
|   | 20–25 KD | 44 ± 6 | 6.7 |
|   | 25–30 KD | 52 ± 7 | 0 |
|   | 30–45 KD | 52 ± 3 | 0 |
|   | ≧45 KD | 51 ± 4 | 0 |

[a]E-IgE referes to bovine erythrocytes coated with IgE PS
[b]Mean ± 1 SD of 20 determinations
[c]$P \leq 0.01$ (paired T test after angular transformation)
[d]Mean ± 1 SD of 2 experiments
[e]The effluents and eluates are obtained as described for Mab-94-Affigel in Example 15 and are used at a dilution of 1:10 after dialysis against HBSS

Immunoregulatory Activity of Colostrum IRE-bfs

The colostrum preparations are added at final concentrations ranging from 1 to 1000 mcg/ml to B lymphocyte cultures derived from 39 allergic human donors. After one week culture in the absence of colostrum the spontaneous secretion of IgE was greater than 400 pg/ml in 13 cases (range: 400 to 11,600 pg/ml), whereas, in 14 cases it was comprised between 150 and 400 pg/ml and in 12 cases it was not detectable. In all but one experiment (Table II), colostrum suppressed in a dose dependent fashion the synthesis of IgE without altering the production of IgM. At final concentrations of 10 to 100 mcg/ml, colostrum completely suppressed IgE synthesis in the cultures secreting less than 400 pg/ml of IgE (data not shown). Under the same conditions, a fifty percent inhibition of IgE synthesis was noted in the cultures secreting more than 400 pg/ml (Table II). The IgE suppressive activity of colostrum can be absorbed on IgE-Sepharose 4B but not on IgG-Sepharose 4B, indicating that it is mediated by IgE-bfs (Table III).

Western Blot Analysis: One band with an apparent MW of 14–15 KD bound to radiolabeleld IgE but not to radiolabelled IgG, IgA and IgM. The specificity of this band was further documented by showing that it was not detected if the colostrum had been preadsorbed on IgE-Sepharose. The same pattern was observed if the colostrum was boiled for 3 min in Laemmli buffer. Hence, it is concluded that colostrum IgE-bfs are resistant to reducing agents (like SDS) and to ebullition.

TABLE II

Influence of colostrum on the spontaneous secretion of IgE by B lymphocytes from allergic individuals

| Expt. # | | Cultures Supplemented With — | Colostrum (10 or 100 μg/ml) | % Suppression |
|---|---|---|---|---|
| 1 | IgE | 700[a] | 0 | 100 |
|   | IgM | 30 | 43 | |
| 2 | IgE | 1750 | 750 | 57.2 |
|   | IgM | 12 | 9 | |
| 3 | IgE | 650 | 150 | 73 |
|   | IgM | 44 | 44 | |
| 4 | IgE | 700 | 100 | 85.8 |
|   | IgM | 38 | 38 | |
| 5 | IgE | 1100 | 700 | 46.4 |
|   | IgM | 27 | 27 | |
| 6 | IgE | 6900 | 5800 | 16 |
|   | IgM | 30 | 30.5 | |
| 7 | IgE | 4300 | 5500 | 0 (−27) |
|   | IgM | 49 | 54 | |
| 8 | IgE | 1300 | 660 | 49.3 |
|   | IgM | 52 | 41 | |
| 9 | IgE | 7700 | 5200 | 32.5 |
|   | IgM | 62 | 60 | |
| 10 | IgE | 11,600 | 5200 | 53.2 |
|   | IgM | 110 | 85 | |
| 11 | IgE | 800 | 200 | 75 |
|   | IgM | 7 | 5 | |
| 12 | IgE | 4100 | 2200 | 46.4 |
|   | IgM | 45 | 52 | |
| 13 | IgE | 440 | 0 | 100 |
|   | IgM | 80 | 76 | |
| | IgE (pg/ml): | 3273 ± 967 | 2061 ± 666 | 56.5 ± 8.3 |
| | IgM: | 40.5 ± 8.0 | 38.8 ± 6.2 | |

[a]Results are expressed as the net IgE (pg/ml) or IgM (ng/ml) synthesis; mean values of duplicate cultures. Variation between the replicates is less than 20%.

TABLE III

IgE-Suppressing Activity is due to IgE-BFs

| | IgE (pg/ml) | |
|---|---|---|
| Added to Cultures | Expt. 1 | Expt. 2 |
| — | 1240 ± 240 | 890 ± 135 |
| Colostrum | 550 ± 180 | 200 ± 50 |
| Colostrum adsorbed on IgE-Sepharose | 1170 ± 290 | 1150 ± 230 |
| Colostrum adsorbed on IgE-Sepharose | 690 ± 210 | 380 ± 90 |

Adsorbed and non-adsorbed colostrum were used at 100 μg/ml; mean ± 1 SD of duplicate cultures.

EXAMPLE 2

Pharmaceutical preparations (parenteral administration)

500 mg of lyophilized colostrum preparation containing IgE-bf are dissolved in 600 ml of 5N human serum albumin. The resulting, solution is passed through a bacteriological filter and the filtered solution is subdivided under aseptic conditions into 100 vials each containing 5 mg of active compound. The vials which are suitable for parenteral administration are preferably stored in the cold, for example at −20° C.

In the same manner, vials containing 1 or 10 mg, may be prepared by using 100 or 1000 mg, respectively, of the above colostrum preparation.

REFERENCES

1. Ishizaka, K. Regulation of IgE synthesis, Annual Rev. of Immunol. 1984, 2:152.
2. Katz, D.H. and Maceletti, J.F., (1983) Regulation of the IgE antibody system in humans and experimental animals. Progress in Immunology, V, ed. Y. Yamamurs and T. Toda, Acad. Press, p. 465.
3. Sarfati, M., Rector, E., Rubio-Trujillo, M., Wong, K., Sehon, A.H. and Delespesse, G. In vitro synthesis of IgE by binding factors secreted by RPMI 8866 lymphoblastoid B cells of human lymphocytes. II. Enhancement of the spontaneous IgE synthesis by IgE. Immunology 1984, 53:197.

4. Huff, T.F. and Ishizaka, K. Formation of IgE-binding factors by human T cell-hybridomas. Proc. Natl. Acad. Sci. (USA) 1984, 81:1514.
5. Sandberg, K., Provost, T. and Ishizaka, K. IgE-binding factors in atopic eczema. 1983. In Proceed. of XI Int. Congress Allergy Clin. Immunol., MacMillan, p. 105.
6. Beer, A.E., Billingham, R.E. and Head, J.R. Natural transplantation of leukocytes during suckling. Transplant. Proc. 1975, 7:366.
7. Schlesinger, J.J. and Covelli, H.D. Evidence for transmission of lymphocyte responses to tuberculin by breast-feeding. Lancet 1977, 2:529.
8. Mohr, J.A. The possible induction and/or acquisition of cellular hypersensitivity associated with ingestion of colostrum. J. Pediat. 1973, 82:1002.
9. Cruz, J.R., Garcia, B. and Urrutia, J.J. and Hanson, L.A. Food antibodies in milk from guatemalan woman, J. Pediat. 1981, 93:600.
10. Frick, O.L., German, D. and Mills, J. Development of allergy in children. I. Association with virus infection. J. Allergy Clin. Immunol. 1979, 63:228.
11. Crago, S.S. and Mestecky, J. Immunoinhibitory elements in human colostrum. Surv. Immunol. Res. 1983, 2:164.
12. Kjellman, N.-I.M. and Croner, S. Cord blood IgE determination for allergy prediction. A follow-up to seven years of age in 1,651 children. Annals of Allergy 1984, 53:167.
13. Jarret, E.E.E. and Hau, E. Selective suppression of IgE antibody responsiveness by material influence. Nature (Lond) 1973, 280:145.
14. Roberts, S.A. and Turner, M.W. Specific suppression of rat IgE responses with milk from immunized females and with feeds of serum antibody. Immunology 1983, 48:195.
15. Richie, E.R., Bass, R., Meistrich, M.L. and Dennison, D.K. Distribution of T lymphocytes subsets in human colostrum. J. Immunol. 1982, 129:1116.
16. Parmely, M.J., Beer, A. and Billingham, R.E. In vitro studies on the T-lymphocyte populations of human milk. J. Exp. Med. 1976, 144:358.

I claim:

1. IgE binding factors having IgE suppressor activity isolated from human colostrum.

2. IgE binding factors of claim 1, wherein said factors
   (a) are polypeptides having a molecular weight of between 10 and 25 kilo-dalton as determined by chromatography on a calibrated Sephadex G75 column;
   (b) block the binding of IgE to cells bearing receptors for IgE;
   (c) suppress in a dose dependent fashion the synthesis of IgE without altering the production of IgM by B lymphocytes of allergic human donors; and
   (d) bind to IgE but not to IgG, IgM or IgA.

3. IgE binding factors of claim 1, essentially free of other human colostrum polypeptides having a molecular weight of less than 10kD and greater than 25kD.

4. IgE binding factors of claim 1, essentially free of non-polypeptide ingredients of human colostrum.

5. IgE binding factors of claim 2, having a molecular weight in the range of about 14–kD.

* * * * *